United States Patent [19]

Armand et al.

[11] Patent Number: 4,556,616

[45] Date of Patent: Dec. 3, 1985

[54] TETRAKIS TRIALKYL SILOXY ALANATES OF ALKALI METALS, THEIR SOLID SOLUTIONS WITH PLASTIC MATERIALS AND THEIR USE FOR THE CONSTITUTION OF CONDUCTOR ELEMENTS FOR ELECTROCHEMICAL GENERATORS

[75] Inventors: Michel B. Armand, Nancy, France; Fouzia El Kadiri Cherkaoui el Moursli, Sale, Morocco

[73] Assignees: Agencie Nationale de Valorisation de la Recherche, Paris; Societe Nationale Elf Aquitaine, Courbevoie, both of France

[21] Appl. No.: 500,194

[22] Filed: Jun. 1, 1983

[30] Foreign Application Priority Data

Jun. 1, 1982 [FR] France ................. 82 09539

[51] Int. Cl.$^4$ .............................................. H01M 6/18
[52] U.S. Cl. .................................. 429/192; 252/62.2; 252/182.1
[58] Field of Search ............. 429/192; 252/62.2, 182.1

[56] References Cited

U.S. PATENT DOCUMENTS 3,373,178  3/1968  Schmidt et al. ................. 260/429 R
4,281,072  7/1981  Wetton et al. ..................... 252/62.2
4,303,748 12/1981  Armand et al. ...................... 429/192

FOREIGN PATENT DOCUMENTS 0937557 12/1955 Fed. Rep. of Germany .

OTHER PUBLICATIONS

Myshlyneva et al., "Study of the Reaction of Trimethylchlorosilane with an Aqueous Alkaline Solution of Sodium Aluminate", Chemical Abstracts, vol. 68, No. 3, Jan. 15, 1968, p. 1257.

*Primary Examiner*—Donald L. Walton
*Attorney, Agent, or Firm*—Weiser & Stapler

[57] ABSTRACT

The invention relates to novel ionic compounds incorporable with polymers of which the monomer units comprise at least one hetero-atom, particularly oxygen or nitrogen, adapted to form bonds of the donor-acceptor type with the cation of the ionic compound, the solid solutions obtained being useful for forming the electrolyte of an electrochemical generator. These ionic compounds are represented by the formula

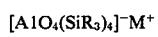

in which the groups R are aprotic hydrocarbon radicals, that is to say radicals which are non-donors of protons, and M is an alkali metal.

28 Claims, No Drawings

TETRAKIS TRIALKYL SILOXY ALANATES OF ALKALI METALS, THEIR SOLID SOLUTIONS WITH PLASTIC MATERIALS AND THEIR USE FOR THE CONSTITUTION OF CONDUCTOR ELEMENTS FOR ELECTROCHEMICAL GENERATORS

The invention relates to a novel ionic compound having the formula $M^+X^-$, in which M is a cation derived from an alkali metal or ammonium ion, and $X^-$ is an anion having a behaviour similar to that of a strong acid. The invention relates more particularly to ionic compounds which can be dissolved within a macromolecular material formed at least in part of one or several homo and/or copolymers derived from one or several monomeric units including at least one hetereoatom, particularly oxygen or nitrogen, adapted to form bonds of the donor-acceptor type with the cation of the ionic compound. More particularly still, the invention relates to ionic compounds of this type, which can be dissolved in at least certain of plastic materials, such as those which have been described in European Patent Application No. 0013 199 entitled "Electrochemical generators for the production of current and novel materials for their manufacture."

The invention also relates to the solid solutions themselves, which have thus been obtained and which, like those more particularly described in the above-said European patent application, are endowed with a sufficient cationic conductivity to be useful for the production of solid electrolytes for the constitution of electrochemical generators, preferably rechargeable. These solid solutions are again useful for the constitution of electrochemical generator electrodes, when these electrodes are constituted by the product of agglomeration into a composite mass of the active material of the latter and, if necessary, of a compound inert to electronic conduction, on the one hand and of the above solid solution, on the other hand.

It is self-evident that the solid solutions according to the invention may resort to any other type of plastic material to the extent that their characteristics of reciprocal solubility are sufficient for obtaining a solid solution having a cationic conductivity of $10^{-5}$ ohms$^{-1} \times$ cm$^{-1}$, preferably at at temperature not exceeding 130° C.

The ionic compounds according to the invention can be represented by the following general formula $$[AlO_4(SiR_3)_4]^- M^+$$

in which the R groups are aprotic hydrocarbon radicals, that is to say radicals which are non-donors of protons, and M is an alkali metal.

The hydrocarbon groups are selected from among those which enable the ionic compound thus formed to form mutual solid solutions with plastic materials, more particularly with compounds of the polyether type, such as have been defined in the above said European patent application or again with plastic materials formed of hydrocarbon molecules, bearing side chains of the polyether type.

The R groups contain a number of carbon atoms which will generally be less than 15. Preferably, they are constituted by alkyl groups comprising up to 4 carbon atoms, the terminal metal group being, if necessary, replaced by a phenyl group.

In other words the groups R constitute alkyl or aralkyl groups. They are identical or different from one another whether within the same trialkylsiloxy group or from one trialkylsiloxy group to the other. In the first case, and when one of the R groups contains an aryl or aralkyl group, the other two groups of the same trialkylsiloxy group will in general be constituted by alkyl radicals. In accordance with an advantageous variation of the invention, certain of the carbon atoms of these hydrocarbon groups are replaced by hetero-atoms such as oxygen, sulphur or nitrogen atoms.

The compounds thus obtained, will, in the following, be named "tetrakis-trialkylsiloxy alanates of alkali metals".

The latter compounds may be prepared by a process consisting of reacting a mixed aluminium halide and the desired alkali metal with a trialkyl siloxy derivative of a metal under reaction conditions enabling the precipitation of the halide of the latter metal. It is possible to resort to any inert aprotic solvent corresponding to these conditions, particularly THF.

Below is described the principle of the reaction applied to the production of lithium tetrakis(trimethyl siloxy)alanate of the formula:

$$Li^+[(CH_3)_3SiO]_4Al^-$$

The exchange reaction used is:

$$LiAlCl_4 + 4Na(CH_3)_3SiO \longrightarrow$$

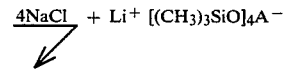

$$4NaCl\downarrow + Li^+[(CH_3)_3SiO]_4Al^-$$

CONDITIONS OF THE REACTION

In solution in THF under a nitrogen atmosphere; ordinary temperature.

The stoichiometric amounts of the compounds are weighed in a glove box and dissolved separately in tetrahydrofurane. The immediate appearance of a precipitate (NaCl) is observed after mixing the solutions with stirring.

In order to remove all traces of sodium ions from the reaction medium due to a possible excess of silanate, lithium chloride is added to displace the equilibrium according to the equation $$(CH_3)_3SiONa + LiCl \longrightarrow NaCl\downarrow + Li(CH_3)_3SiO$$

Finally the compound $$Li^+[(CH_3)_3SiO]_4Al^-$$

is obtained after filtration and evaporation of the solvent.

The ionic compounds according to the invention have quite satisfactory mutual dissolution qualities with poly(propylene oxide) and even, for compounds in which the R groups are constituted by hydrocarbon chains of short length, with poly(ethylene oxide). The solid solutions obtained have a cationic conductivity enabling their use as electrolyte materials for electrochemical generators, preferably of the rechargeable type, whose preferred characteristics are recalled below.

It relates therefore to the novel materials with ionic conduction, particularly cationic which have thus been obtained, more particularly a novel polymeric solid electrolyte constituted at least in part by a solid solution of one or several of the ionic compounds according to the invention, entirely dissolved within a macromolecular material formed at least in part by a polymer, whose monomer units (of one or several types) include at least one hetero-atom, particularly oxygen or nitrogen, adapted to form bonds of the donor-acceptor type with the cation of the ionic compound.

Preferably, the ratio of the number of hetereo-atoms derived from the one or more monomeric units of said polymer to the number of atoms of the alkali metal of said ionic compound is comprised between 4 and 30, particularly 4 and 16. It is self-evident that the proportion of the ionic compound dissolved must be compatible with its solubility level in the selected polymer.

The alkali metal is preferably lithium or sodium.

The preferred plastics materials in which the ionic compounds according to the invention are placed in solution, are homo and/or copolymers derived from monomeric units represented:
either by the following formula

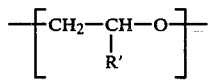

in which R' represents a hydrogen atom or one of the group Ra, —CH$_2$—O—Ra, —CH$_2$—O—Re—Ra, —CH$_2$—N=(CH$_3$)$_2$, with Ra representing an alkyl or a cycloalkyl radical including particularly 1 to 16, preferably 1 to 5 carbon atoms, Re representing a polyether radical of the general formula

p having a value of 1 to 100, particularly from 1 to 2, or by the following formula:

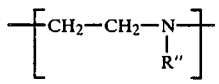

in which R" represents Ra, —Re—Ra, with Ra and Re having respectively one of the above-indicated meanings,
or by the following formula:

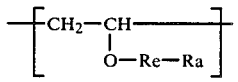

in which Ra and Re have respectively one of the above indicated meanings,
or by the formula:

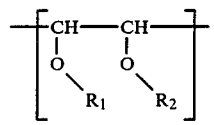

in which R$_1$ and R$_2$ are identical or different and each represent one of the groups Re, Re—Ra with the above meanings, and Re can then represent also a poly-ether of the formula

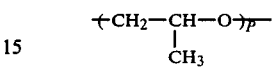

The preparation of the polymeric solid electrolyte may be carried out by the dissolving, in a solvent such as acetonitrile, or again methanol, of the polymer and of the ionic compound, then removal of the solvent, it being understood that a proporation of ionic compound is used less than that for which the solubility threshold is reached.

It is also possible to use any known method not resorting to solvent, for example by dissolving in the molten polymer.

The solid electrolytes produced according to the invention, find particularly advantageous application for the production of both primary and secondary electrochemical generators.

In particular, a solid electrolyte comprising in solution an ionic compound of the above-indicated type, may be associated with a negative electrode, constituted by a material adapted to provide the alkali ion corresponding to the metal of the ionic compound selected and a positive electrode adapted to incorporate the atoms of this metal. It is possible, for example, to provide a negative electrode constituted by the same alkali metal in the form of an alloy, or constituted by an intermetallic compound, an insertion compound or the like. For the positive electrode, it is possible to use any material whose crystalline structure enables the insertion of alkali metals. For example may be mentioned the chalcogenides which permit the diffusion of the alkali metal into their structure. It is possible again, as regard other examples of suitable materials for the formation of the positive electrodes, to refer to the already mentioned European patent application.

It is also possible to produce one of the electrodes, for example the positive one, by forming a composite from the active material of the latter and from these solid solution of the ionic compound, within the same macromolecular material. This composite can also include a compound inert to electronic conduction. It is also possible to resort, to constitute such electrodes and apart from the choice of the cationic compound, to the same methods of constitution as those described in European patent application No. 0013 199.

When these generators are constructed, it is observed that the novel electrolyte according to the invention has the advantage that the anion of the salt or ionic compound in solution is inert with respect to the majority of electrode materials that it is possible to use. This property enables a large number of cycles and stable storage. In addition, this chemical inertness confers on the generators which are thus constructed a very good resistance to thermal shock.

Other characteristics and advantages of the polymeric solid electrolytes according to the invention will appear in the embodiments which follow it being understood that these examples are in no way limiting.

These examples are indicative, particularly of the chemical and/or physical properties of particular ionic compounds of the invention and, in relationship with certain plastic electrolytes constituted with certain of some of them, are indicative of the values of temperatures in °C. for which the conductivities are equal to about $10^{-5}\Omega^{-1}cm^{-1}(T\sigma 10^{-5})$, even to $10^{-4}\Omega^{-1}cm^{-1}(T\sigma 10^{-4})$. These measurements have been carried out in vacuum, so as to remove any trace of moisture and/or of solvent.

In all these examples, the macromolecular material is, as the case may be, a poly-(ethylene oxide) (POE) or a poly-(propylene oxide) of molecular weights equal or higher than 900,000. The electrolyte has been obtained by dissolving 1 g of this poly-(ethylene oxide) or this poly-(propylene oxide) in 35 ml of acetonitrile, then the addition of the ionic compound, to obtain atomic ratios O/Li or O/Na which are indicated below.

The solution so obtained is cast on a polytetrafluorethylene support, to a thickness of 5 mm, then stoved at 60° C. for 3 hours.

The conductivity measurements were done by the techniques described by E. Schouler et al, J. Chim. Phys.9 1309/16 (1973) and D. Ravaine et al, J. Chim. Phys.5 (93-70 (1974).

SYNTHESIS OF THE COMPOUND

Tetrakis(trimethylsiloxy)alanate of the formula:

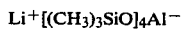

The exchange reaction used is:

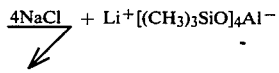

REACTION CONDITIONS

Reaction in THF under a nitrogen atmosphere: ordinary temperature.

The stoichiometric amounts of the compounds are weighed in a glove box and dissolved separately in tetrahydrofurane. The immediate appearance of a precipitate (NaCl) is observed after mixing the solutions with stirring.

In order to remove all traces of the sodium ion from the reaction medium due to a possible excess of silanate, lithium cloride is added to displace the equilibrium according to:

After this, a filtration followed by removal of the solvent in a rotary evaporator enables the production of the compound:

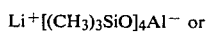

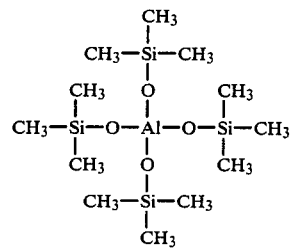

This compound is a microcrystalline white solid, very soluble in polar solvents (THF, DMSO, etc.). It is also soluble in certain non-polar solvents (benzene, toluene, carbon tetrachloride), remarkable properties for an ionic compound. It melts about 185° C. It must be handled protected from moisture.

It has, on the level of solubility in polymers, excellent compatibility with PPO. The electrochemical amounts of the solid solutions obtained, make them particulary useful for the constitution of ionic conductors (particularly electrolytes) of electrochemical generators whose constitution has been recalled above. The following conductivity results bear witness to this

| O/Li | to $10^{-5}$ | to $10^{-4}$ |
|------|-------------|-------------|
| 8    | 114         | 130         |
| 12   | 50          | 128         |

It is the same for solid solutions obtained with PPO and

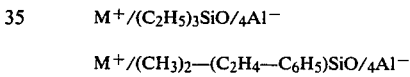

with

We claim:

1. An ionic compound of the formula:

$[AlO_4(SiR_3)_4]^-M^+$ in which:
   R is an aprotic hydrocarbon group and at least one R is an aralkyl group, and
   M is an alkali metal.

2. The compound according to claim 1, wherein R contains less than 15 carbon atoms.

3. The compound according to claim 1, wherein R is alkyl and aralkyl groups containing less than 15 carbon atoms.

4. The compound according to claim 3, wherein said R which is alkyl comprises up to 4 carbon atoms.

5. The compound according to claim 1, wherein R is an alkyl and aralkyl groups containing less than 15 carbon atoms and wherein R is a phenylalkyl group with said alkyl group having up to 3 carbon atoms and the other two R groups being alkyl groups comprising up to 4 carbon atoms.

6. Material having ionic conduction which comprises at least in part a solid solution of at least one ionic compound according to any one of claims 2, 3, 4 and 5 entirely dissolved within a macromolecular material formed at least in part by a polymer having monomer units which comprise at least one hetero-atom, adapted to form bonds of the donor-acceptor type with the cation of the ionic compound.

7. The material with ionic conduction, which comprises at least in part by a solid solution of at least one ionic compound according to any one of claims 1, 2, 3, 4 or 5 entirely dissolved within poly(ethylene oxide) or poly(propylene oxide).

8. The material with ionic conduction according to claim 7, wherein the ratio of the number of hetero-atoms derived from the monomer units of poly(ethylene oxide) or poly(propylene oxide) to the number of atoms of the alkali metal of said ionic compound is comprised between 4 and 30.

9. The material with ionic conduction according to claim 7, wherein the ratio of the number of hetero-atoms derived from the monomer units of said poly(ethylene oxide) or poly(propylene oxide) to the number of atoms of the alkali metal of said ionic compound is comprised between 4 and 16.

10. Material having ionic conduction which comprises at least in part a solid solution of at least one ionic compound of the formula:

$$[AlO_4(SiR_3)_4]^- M^+$$

in which:
R is an aprotic hydrocarbon group, and
M is an alkali metal;
entirely dissolved within a macromolecular material formed at least in part by a polymer having monomer units which comprise at least one hetero-atom adapted to form bonds of the donor-acceptor type with the cation of the ionic compound.

11. Material having ionic conduction which comprises at least in part one ionic compound of the formula:

$$[AlO_4(SiR_3)_4]^- M^+$$

in which:
R is an aprotic hydrocarbon group and at least one R is an aralkyl group, and M is an alkali metal,
entirely dissolved within a macromolecular material formed at least in part by a polymer having monomer units which comprise at least one hetero-atom adapted to form bonds of the donor-acceptor type with the cation of the ionic compound.

12. The material with ionic conduction according to claim 11 or 10, wherein the hetero-atom is oxygen or nitrogen.

13. The material with ionic conduction according to claim 11 or 10, wherein the ratio of the number of hetero-atoms derived from the monomer units of the above said macromolecular material to the number of atoms of the alkali metal of said ionic compound is comprised between 4 and 30.

14. The material with ionic conduction according to claim 11 or 10, wherein the ratio of the number of hetero-atoms derived from the monomer units of said macromolecular material to the number of atoms of the alkali metal of said ionic compound is comprised between 4 and 16.

15. An electrochemical generator for producing electrical current, comprising a negative electrode and a positive electrode separated from each other by an electrolyte which comprises macromolecular material formed at least in part by a polymer whose monomer units include at least one hetero atom adapted to form bonds of the donor-acceptor type with a cation of an ionic compound, and said macromolecular material having a solid solution of an ionic compound of the formula:

$$[AlO_4(SiR_3)_4]^- M^+$$

wherein:
R is an aprotic hydrocarbon group, and
M is an alkali metal.

16. The generator according to claim 15 wherein R contains less than 15 carbon atoms.

17. The generator according to claim 15 wherein R is an alkyl or aralkyl group containing less than 15 carbon atoms.

18. The generator according to claim 15 wherein R is an alkyl group comprising up to 4 carbon atoms.

19. The generator according to claim 15 wherein R is an alkyl or aralkyl group containing less than 15 carbon atoms and wherein R is a phenylalkyl group, with said alkyl group having up to 3 carbon atoms and the other two R groups being alkyl groups comprising up to 4 carbon atoms.

20. The generator compound according to claim 15 wherein said ionic compound is one tetrakis(trimethylsiloxy)alanate.

21. The generator according to claim 15 wherein said macromolecular material is poly(ethylene oxide) or poly(propylene oxide).

22. An electrochemical generator for producing electrical current, comprising a negative electrode and a positive electrode separated from each other by an electrolyte which comprises macromolecular material formed at least in part by a polymer whose monomer units include at least one hetero atom adapted to form bonds of the donor-acceptor type with a cation of an ionic compound, and said macromolecular material having a solid solution of an ionic compound of the formula:

$$[AlO_4(SiR_3)_4]^- M^+$$

wherein:
R is an aprotic hydrocarbon group and at least one R is an aralkyl group and
M is an alkali metal.

23. The electrochemical generator of claim 22 wherein said positive electrode also comprises said electrolyte material.

24. The electrochemical generator of claim 22 wherein said negative electrode comprises a material adapted to supply a corresponding alkali ion to the ionic compound of said solid solution and said positive electrode is adapted to incorporate the atoms of said metal.

25. The electrochemical generator of claim 22 wherein said macromolecular material is poly(ethylene oxide) or poly(propylene oxide).

26. An electrode structure in which the electrode material of said electrode structure comprises solid macromolecular electrolyte material formed at least in part by an electrolyte which comprises macromolecular material formed at least in part by a polymer whose monomer units include at least one hetero atom adapted to form bonds of the donor-acceptor type with a cation of an ionic compound, and said macromolecular material having a solid solution of an ionic compound of the formula:

$$[AlO_4(SiR_3)_4]^- M^+$$

wherein:
R is an aprotic hydrocarbon group, and
M is an alkali metal.
27. The electrode structure of claim 26 wherein said macromolecular material is poly(propylene oxide) or poly(ethylene oxide).
28. The electrode structure of claim 26 wherein said ionic compound is tetrakis(trimethylsiloxy alanate).

* * * * *